(12) United States Patent
Pollock et al.

(10) Patent No.: US 9,791,418 B2
(45) Date of Patent: Oct. 17, 2017

(54) SYSTEM AND METHOD FOR MONITORING THE STRUCTURAL HEALTH OF ROTATING ELEMENTS

(71) Applicant: ACELLENT TECHNOLOGIES, INC., Sunnyvale, CA (US)

(72) Inventors: Patrick Joseph Pollock, Oakland, CA (US); Howard Hungchi Chung, San Jose, CA (US); Roger Huang, Mountain View, CA (US); Fu-Kuo Chang, Stanford, CA (US); Irene Li, Stanford, CA (US); Jeffrey Dean Bergman, Santa Clara, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 461 days.

(21) Appl. No.: 14/064,001

(22) Filed: Oct. 25, 2013

(65) Prior Publication Data

US 2014/0116145 A1    May 1, 2014

Related U.S. Application Data

(60) Provisional application No. 61/719,332, filed on Oct. 26, 2012.

(51) Int. Cl.
| | | |
|---|---|---|
| G01N 29/24 | (2006.01) | |
| G01N 29/22 | (2006.01) | |
| G01N 29/27 | (2006.01) | |

(52) U.S. Cl.
CPC .......... *G01N 29/225* (2013.01); *G01N 29/27* (2013.01); *G01N 2291/105* (2013.01); *G01N 2291/2626* (2013.01)

(58) Field of Classification Search
None
See application file for complete search history.

(56) References Cited

U.S. PATENT DOCUMENTS

| | | | | |
|---|---|---|---|---|
| 4,453,409 | A | * | 6/1984 | Naumann et al. ............ 73/639 |
| 4,507,645 | A | * | 3/1985 | Kehl ........................... 340/685 |
| 4,562,738 | A | * | 1/1986 | Nakayama et al. ........... 73/622 |
| 5,436,988 | A | * | 7/1995 | Narendran ..................... 385/26 |
| 8,042,402 | B2 | * | 10/2011 | Brown et al. ................. 73/756 |
| 2004/0169434 | A1 | * | 9/2004 | Washington et al. ....... 310/232 |

FOREIGN PATENT DOCUMENTS

| | | | |
|---|---|---|---|
| JP | 10-124787 | * | 5/1998 |
| JP | 2003166875 | * | 6/2003 |

* cited by examiner

*Primary Examiner* — Robert R Raevis
(74) *Attorney, Agent, or Firm* — Innovation Counsel LLP

(57) ABSTRACT

A structural health monitoring system capable of maintaining electrical contact with sensors affixed to a rotating structure. One such structural health monitoring system comprises a rotatable structure, a plurality of sensors each affixed to the rotatable structure, and an interface. The interface has an inner housing and an outer housing, and maintains a plurality of individual electrical connections, each of the individual electrical connections being an electrical connection between one of the sensors and an electrical contact maintained on the outer housing, the electrical connections configured to be maintained during rotation of the structure. The inner housing is affixed to the structure and the outer housing is rotationally coupled to the inner housing, so that the inner housing is free to rotate with respect to the outer housing during rotation of the structure and the sensors, while maintaining the electrical connections.

18 Claims, 3 Drawing Sheets

SYSTEM AND METHOD FOR MONITORING THE STRUCTURAL HEALTH OF ROTATING ELEMENTS

This application claims priority to, and the benefit of, U.S. Provisional Application No. 61/719,332, filed on Oct. 26, 2012, the entire content of which is hereby incorporated by reference.

BRIEF DESCRIPTION

This invention relates generally to structural health monitoring (SHM). More specifically, this invention relates to systems and methods for monitoring the structural health of rotating elements.

BACKGROUND

Rotating elements, such as shafts and the like, have historically posed challenges to structural health monitoring systems. Rotation has made it difficult to place sensors directly on the rotating elements, as maintaining a reliable electrical connection to these sensors during rotation has proven challenging. Remote sensing methods have also not been sufficiently developed to allow for monitoring without contacting the rotating element.

SUMMARY

The invention can be implemented in a number of ways, such as by a structural health monitoring system.

In one embodiment, a structural health monitoring system comprises a rotatable structure, a plurality of sensors each affixed to the rotatable structure, and an interface having an inner housing and an outer housing. The interface maintains a plurality of individual electrical connections, each of the individual electrical connections being an electrical connection between one of the sensors and an electrical contact maintained on the outer housing, the electrical connections configured to be maintained during rotation of the structure. The inner housing may be affixed to the structure and the outer housing may be rotationally coupled to the inner housing, so that the inner housing is free to rotate with respect to the outer housing during rotation of the structure and the sensors, while maintaining the electrical connections.

The interface can further comprise a plurality of conductive brushes, each conductive brush electrically connected between a respective one of the electrical contacts and one of the sensors.

Each conductive brush can be affixed to the inner housing, and each conductive brush may have one or more conductive bristles placed in frictional contact with the outer housing so as to allow the outer housing to rotate with respect to the inner housing while the each conductive brush maintains an electrical connection between its respective sensor and its respective electrical contact.

Each electrical connection may further comprise a conductive trace connected between its respective sensor and its respective conductive brush.

Each of the conductive bristles may be a metal bristle.

Each conductive brush may be electrically connected to its respective electrical contact so as to be attached to the outer housing, and each conductive brush may have one or more conductive bristles placed in frictional contact with the inner housing so as to allow the outer housing to rotate with respect to the inner housing while the each conductive brush maintains an electrical connection between its respective sensor and its respective electrical contact.

Each electrical connection may further comprise a conductive trace connected between its respective sensor and its respective conductive brush.

The sensors may be piezoelectric transducers configured to transmit stress waves through the structure and to detect stress waves generated within the structure.

In another embodiment, a structural health monitoring system may comprise a plurality of sensors configured to be affixed to a structure that can rotate about an axis, and an interface having an inner housing and an outer housing. The interface may maintain a plurality of individual electrical connections between a plurality of terminals on the outer housing and corresponding ones of the sensors. The inner housing may be coupled to the plurality of sensors so as to be configured to rotate about the axis along with the plurality of sensors, so that the inner housing is configured to rotate with respect to the outer housing while maintaining each of the electrical connections.

The interface may further comprise a plurality of conductive brushes, each conductive brush electrically connected between the inner housing and one of the terminals on the outer housing, each of the electrical connections being electrically insulated from each of the remaining electrical connections.

Each conductive brush may be affixed to the inner housing, and each conductive brush may have one or more conductive bristles placed in frictional contact with a portion of the outer housing so as to allow the outer housing to rotate with respect to the inner housing while the each conductive brush maintains one of the electrical connections between its respective sensor and its respective terminal.

Each conductive brush may be electrically connected to its respective terminal so as to be attached to the outer housing, and each conductive brush may have one or more conductive bristles placed in frictional contact with a portion of the inner housing so as to allow the outer housing to rotate with respect to the inner housing while the each conductive brush maintains one of the electrical connections between its respective sensor and its respective terminal.

Other aspects and advantages of the invention will become apparent from the following detailed description taken in conjunction with the accompanying drawings which illustrate, by way of example, the principles of the invention.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings. The various Figures are not necessarily to scale.

DETAILED DESCRIPTION OF EMBODIMENTS OF THE INVENTION

In one embodiment, the invention relates to an SHM system that can monitor a structure while it is rotating. Sensors are attached to the rotatable structure, and connected to an interface unit that is also coupled to the structure. The interface unit has an inner ring and an outer ring, where the inner ring is affixed to the structure. The inner ring has conductive brushes whose bristles extend radially outward to contact a conductive portion of the outer ring. The sensors are connected to each brush, where the bristles provide an electrical connection to a terminal on the outer ring. That is, even when the inner and outer rings rotate with respect to each other, the conductive bristles remain in frictional contact with (i.e., continue to brush against) the outer ring, thus maintaining electrical contact therewith. In this manner, each sensor can maintain an electrical connection to the terminals of the outer ring, even while the structure to which they are attached is rotating. This allows for the structure to be monitored even while it is in operation, thus providing for better real-time monitoring and diagnosis.

Figure 1:
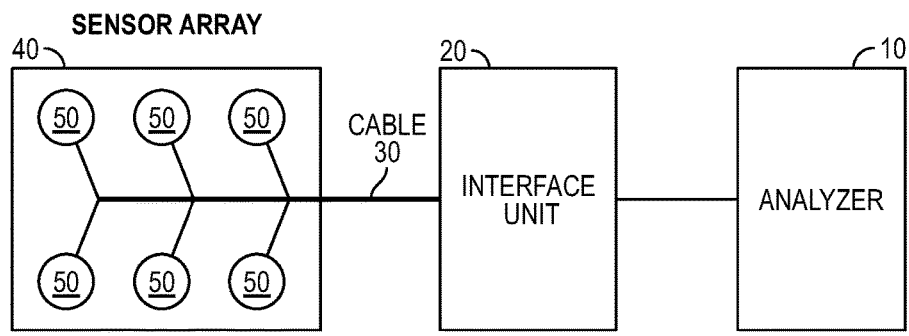
FIG. 1 is a block diagram representation of a system for monitoring rotating elements, according to embodiments of the invention.

A system is provided for conducting structural health monitoring of a rotating part, e.g. rotating shafts and the like. FIG. 1 is a block diagram representation of an embodiment of an exemplary such system, which includes an analyzer 10, interface unit 20, cable 30, and sensor array 40. The sensor array 40 contains any number of sensors 50. The sensors 50 can be any sensors capable of conducting structural health monitoring analysis, but in one example can be known piezoelectric sensors capable of both propagating ultrasonic guided waves in the rotating part for active querying of the part, as well as sensing stress waves in the part or structure. The sensors send/receive signals to/from interface unit 20, which in turn transmits the sent/received signals to analyzer 10 for analysis.

The analyzer 10 includes both power transmission capability for actuating sensors 50 during active querying, as well as analysis capability for analyzing sensed signals from the sensors 50 to determine the health of the rotating part.

Interface unit 20 is configured to be coupled to the rotating part, along with sensor array 40, so that sensor array 40, cable 30, and at least a portion of interface unit 20 each rotate with the rotating part. In one embodiment, the interface unit 20 can be a slip ring with a stationary outer housing and an inner housing rotationally coupled to the outer housing. The inner housing is attached to the rotating part and spins with the part, while the outer housing is fixed (or at least does not move exactly along with the inner housing) and contains electrical and electronic connections for communication with analyzer 10. More specifically, the inner housing can contain a number of interfaces to each of the sensors 50, so that the cable 30 maintains individual connections between each sensor 50 at one end, and a corresponding interface at the other end. The interfaces are each electrically connected to a separate conductive brush, which is in turn positioned to contact a conductive ring in the outer housing. Each ring is positioned so that as its brush spins, it continuously contacts the ring, thus maintaining an electrical contact between a particular sensor 50 and the ring. Each ring is in turn electrically connected to one of the electrical connections in the outer housing, i.e. is connected to the analyzer 10. In this manner, each sensor 50 has its own separate electrical connection to analyzer 10, through the interface unit 20. Further, each electrical connection is insulated from the remaining electrical connections, so that each sensor 50 can be individually controlled by the analyzer 10.

The sensors 50 can each be separately bonded to the rotating part. Alternatively, the sensors 50 can be integrated into a flexible dielectric layer, so that only a single layer need be bonded to the rotating part. Such layers and their arrays of sensors 50 are known, and are further described in, for example, U.S. Pat. Nos. 7,413,919 and 6,370,964, which are both hereby incorporated by reference in their entireties. The flexible layer can include both the array 40 as well as the cable 30, which can each be made as thin flexible layers according to the methods described in the above referenced patents.

In certain embodiments, the sensor array 40 can include a flexible layer in which sensors 50 are incorporated, as shown in FIG. 1 and as described in the above referenced patents. The flexible layer is first attached to a structure in a manner that allows the sensors 50 to detect quantities related to the health of the structure. For instance, the sensors 50 can be configured to detect stress waves propagated within the structure, and to emit electrical signals accordingly. The analyzer 10 then analyzes these electrical signals according to known structural health monitoring methods, to assess various aspects of the health of the structure. For instance, detected stress waves can be analyzed to detect crack propagation within the structure, delamination within composite structures, or the likelihood of fatigue-related failure. Quantities such as these can then be displayed to the user via a display in, or in communication with, analyzer 10.

In one embodiment, the sensors 50 are piezoelectric transducers capable of reacting to a propagating stress wave by generating a voltage signal. Analysis of these signals highlights properties of the stress wave, such as its magnitude, propagation speed, frequency components, and the like. Such properties are known to be useful in structural health monitoring.

The sensors 50 and analyzer 10 can be configured to conduct any type of structural health monitoring. For example, the sensors 50 can query the structure (or passively detect stress waves generated during operation of the rotating part) for detection of fatigue cracks, corrosion, plastic deformation in metallic parts and delaminations, disbonds, and cracking in composite parts, and/or any other quantities of interest in structural health monitoring.

In this manner, embodiments of the invention allow for a network of structural health monitoring sensors 50 to be directly attached to a rotating part, so that the sensors 50 can monitor the structural health of the rotating part during its operation, and in real time.

Accordingly, in one embodiment, the system uses piezoelectric discs to propagate ultrasonic guided waves in the rotating part. The piezoelectric discs can serve as actuators and sensors. A slip ring is used to provide an electrical connection between the sensors on the rotating part and the stationary data acquisition hardware. The piezoelectric discs are embedded in a flexible polyimide film which also contains the wiring for every disc. The polyimide film containing the piezoelectric discs is bonded to the rotating part. The wiring in the polyimide film is routed to a central area for a simple connection to the slip ring.

Figure 2:
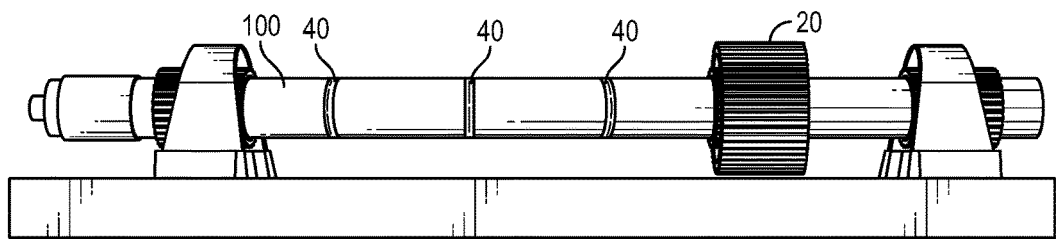
FIGS. 2 and 3 conceptually illustrate the configuration of the system of FIG. 1, implemented on a rotating shaft.
Figure 3:
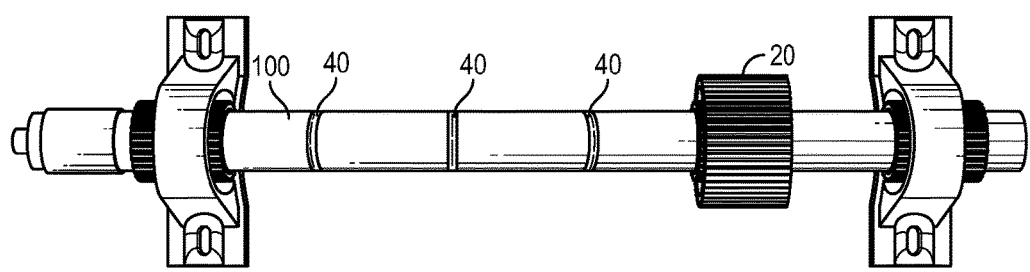

FIGS. 2 and 3 conceptually illustrate the configuration of the system of FIG. 1, implemented on a rotating shaft. The sensor array 40, shown as being incorporated into or onto a flexible layer shaped for affixing to the shaft 100, is bonded to the shaft 100. The interface unit 20 is shown as a slip ring whose inner housing is attached to the shaft 100.

Figure 6:
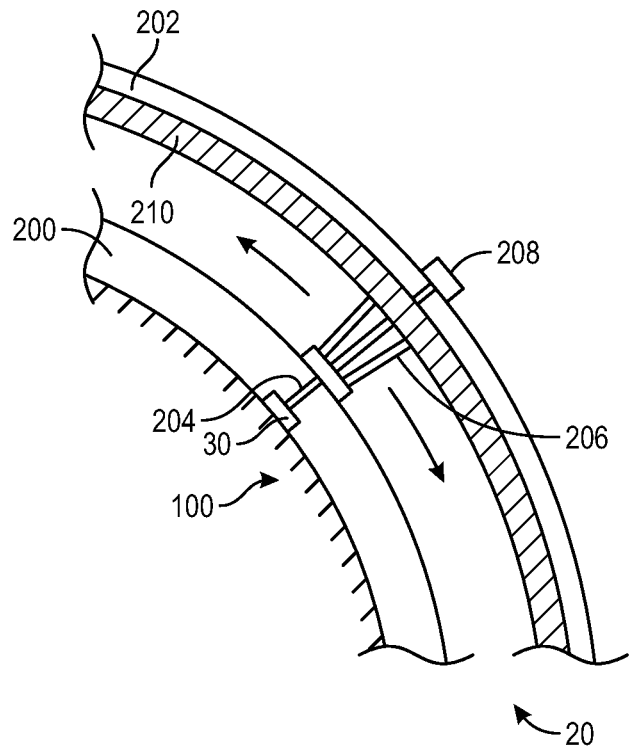
FIG. 6 illustrates a cross-section of an electrical interface unit, that is taken along section I-I of FIG. 2.
Figure 7:
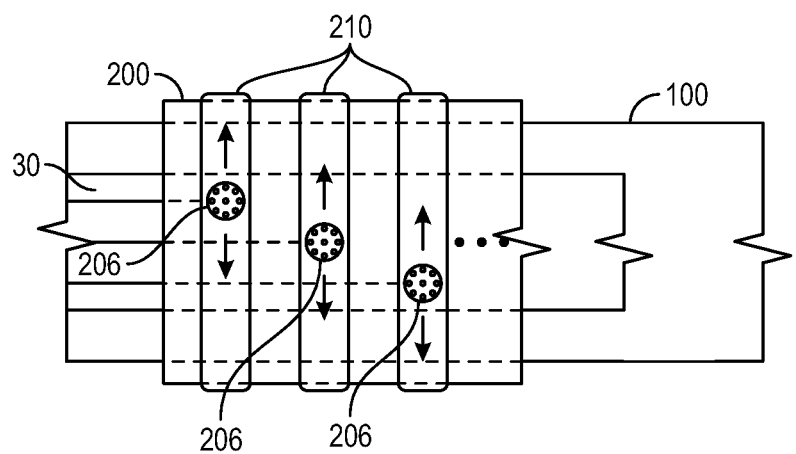
FIG. 7 illustrates a plan view of the inner ring and portions of the outer ring of the electrical interface unit of FIG. 1.

FIGS. 6 and 7 illustrate further details of interface unit 20. FIG. 6 is a cross-sectional view of interface unit 20, and FIG. 7 is a plan view of the inner ring thereof, as well as a portion of the outer ring. More specifically, the slip ring or interface unit 20 has an inner ring 200 and outer ring 202. The inner ring 202 is attached to shaft 100, and rotates therewith. The outer ring 202 is positioned radially outward from the inner ring 200, and is free to rotate independent of inner ring 200, or can be affixed so that it does not rotate. Each of the inner ring 200 and outer ring 202 can be made of any suitable material. For example, each can be made of a steel or other metal that is compatible with the material of the shaft 100.

The inner ring 200 has a number of conductive brushes 206 extending radially outward therefrom, where each brush 206 is connected by cable 30 and wiring 204 to one particular sensor 50. The conductive brush 206 has a number of conductive bristles made of a metal or other conductor, and extends radially outward to contact a conductive collar 210 bonded to outer ring 202. The conductive collar 210 is bonded to the outer ring 202 with an insulating adhesive, or alternatively can have an insulating layer (not shown) placed between itself and the outer ring 202 (or, the outer ring 202 can simply be made of an insulating material). Each conductive collar 210 is electrically connected to a separate terminal 208 on the exterior of outer ring 202, as shown. Leads from analyzer 10 can then be connected to each terminal 208 to transmit/receive electrical signals to/from each sensor 50.

As can be seen from FIG. 7, each sensor 50 is connected to a separate conductive brush 206 which in turn contacts, and is thus electrically connected to, one of the conductive collars 210 of outer ring 202. Thus, a continuous electrical pathway is maintained between each sensor 50 and its associated terminal 208. As the shaft 100 rotates about its major axis (and hence each sensor 50 rotates about the same axis), each brush 206 rotates in the same manner, its bristles frictionally contacting its respective collar 210 and thus maintaining electrical contact therewith. In FIG. 7, note that the collars 210 are connected to, and may be considered part of, outer ring 202.

Embodiments of the invention are not limited to those shown. For example, while the conductive brushes 206 are shown as attached to the inner ring 200, one of ordinary skill in the art will observe that the brushes 206 can instead be attached to the outer ring 202, so that their bristles frictionally contact the inner ring 200. In such a configuration, the inner ring 200 can have a number of collars that are insulated from each other, where each brush 206 contacts one of these collars. Each collar is then placed in electrical contact with one of the sensors 50.

Figure 4:
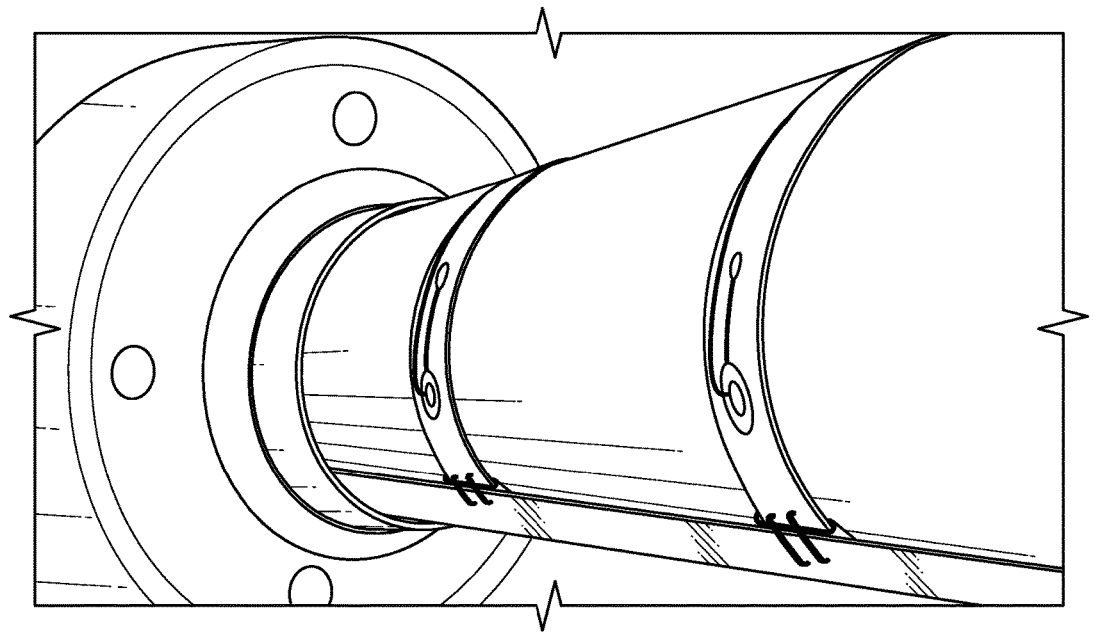
FIGS. 4 and 5 are pictures of an actual implementation of one system exemplifying an embodiment of the invention.
Figure 5:
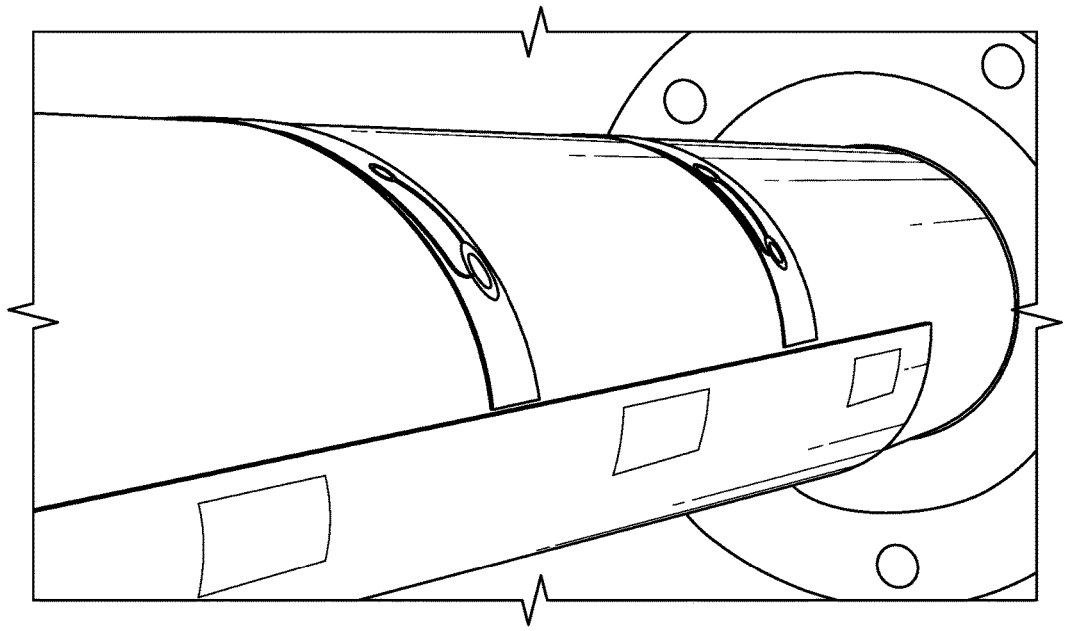

FIGS. 4 and 5 are pictures of an actual implementation of one system exemplifying an embodiment of the invention. Shown is a metallic shaft that rotates, with a PCB-like flexible sensor array layer bonded to the shaft. The flexible layer contains a number of piezoelectric sensors that are thereby placed in communication with the shaft. The slip ring can be seen in the background of FIG. 4, and the sensor layer extends into the slip ring, for electrical contact to the connections maintained in its inner housing.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, the sensors 50 can be arranged in any configuration and number on the rotating part, and can be incorporated into a dielectric layer or individually placed. Also, the various embodiments each have certain features that differ from those of other embodiments, and it is noted that the invention contemplates the mixing and matching of various features as desired. That is, further embodiments can be formed from the selection of various features from different embodiments. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A structural health monitoring system, comprising:
   a rotatable structure;
   a plurality of sensors each affixed to an outer surface of the rotatable structure so as to be able to monitor the structure while said structure rotates; and
   an interface having an inner housing and an outer housing, the interface maintaining a plurality of individual electrical connections, each of the individual electrical connections being an electrical connection between one of the sensors and an electrical contact maintained on the outer housing, the electrical connections configured to be maintained during rotation of the structure;
   wherein the inner housing is affixed to the outer surface of the rotatable structure and the outer housing is rotationally coupled to the inner housing, so that the inner housing is free to rotate with respect to the outer housing during rotation of the structure and the sensors, while maintaining the electrical connections.

2. The structural health monitoring system of claim 1, wherein the interface further comprises a plurality of conductive brushes, each conductive brush electrically connected between a respective one of the electrical contacts and one of the sensors.

3. The structural health monitoring system of claim 2, wherein each conductive brush is affixed to the inner housing, and wherein each conductive brush has one or more conductive bristles placed in frictional contact with the outer housing so as to allow the outer housing to rotate with respect to the inner housing while the each conductive brush maintains an electrical connection between its respective sensor and its respective electrical contact.

4. The structural health monitoring system of claim 3, wherein each electrical connection further comprises a conductive trace connected between its respective sensor and its respective conductive brush.

5. The structural health monitoring system of claim 3, wherein each of the conductive bristles is a metal bristle.

6. The structural health monitoring system of claim 2, wherein each conductive brush is electrically connected to its respective electrical contact so as to be attached to the outer housing, and wherein each conductive brush has one or more conductive bristles placed in frictional contact with the inner housing so as to allow the outer housing to rotate with respect to the inner housing while the each conductive brush maintains an electrical connection between its respective sensor and its respective electrical contact.

7. The structural health monitoring system of claim 6, wherein each electrical connection further comprises a conductive trace connected between its respective sensor and its respective conductive brush.

8. The structural health monitoring system of claim 6, wherein each of the conductive bristles is a metal bristle.

9. The structural health monitoring system of claim 1, wherein the sensors are piezoelectric transducers configured to transmit stress waves through the structure and to detect stress waves generated within the structure.

10. A structural health monitoring system, comprising:
a plurality of sensors configured to be affixed to an outer surface of a structure that can rotate about an axis, so as to be able to monitor the structure while said structure rotates; and
an interface having an inner housing and an outer housing, the interface maintaining a plurality of individual electrical connections between a plurality of terminals on the outer housing and corresponding ones of the sensors;
wherein the inner housing is coupled to the plurality of sensors so as to be configured to rotate about the axis along with the plurality of sensors, so that the inner housing is configured to rotate with respect to the outer housing while maintaining each of the electrical connections.

11. The structural health monitoring system of claim 10, wherein the interface further comprises a plurality of conductive brushes, each conductive brush electrically connected between the inner housing and one of the terminals on the outer housing, each of the electrical connections being electrically insulated from each of the remaining electrical connections.

12. The structural health monitoring system of claim 11, wherein each conductive brush is affixed to the inner housing, and wherein each conductive brush has one or more conductive bristles placed in frictional contact with a portion of the outer housing so as to allow the outer housing to rotate with respect to the inner housing while the each conductive brush maintains one of the electrical connections between its respective sensor and its respective terminal.

13. The structural health monitoring system of claim 12, wherein the interface further comprises a conductive trace connected between its respective sensor and its respective conductive brush.

14. The structural health monitoring system of claim 12, wherein each of the conductive bristles is a metal bristle.

15. The structural health monitoring system of claim 11, wherein each conductive brush is electrically connected to its respective terminal so as to be attached to the outer housing, and wherein each conductive brush has one or more conductive bristles placed in frictional contact with a portion of the inner housing so as to allow the outer housing to rotate with respect to the inner housing while the each conductive brush maintains one of the electrical connections between its respective sensor and its respective terminal.

16. The structural health monitoring system of claim 15, wherein the interface further comprises a conductive trace connected between its respective sensor and its respective conductive brush.

17. The structural health monitoring system of claim 15, wherein each of the conductive bristles is a metal bristle.

18. The structural health monitoring system of claim 10, wherein the sensors are piezoelectric transducers configured to transmit stress waves through the structure and to detect stress waves generated within the structure.

\* \* \* \* \*